(12) United States Patent
Holmes et al.

(10) Patent No.: US 10,416,178 B2
(45) Date of Patent: Sep. 17, 2019

(54) BIOLOGICAL SAMPLE PROCESSING (71) Applicant: Theranos, Inc., Palo Alto, CA (US)

(72) Inventors: Elizabeth A. Holmes, Palo Alto, CA (US); Adrit Lath, Palo Alto, CA (US)

(73) Assignee: Theranos IP Company, LLC, New York, NY (US)

( * ) Notice: Subject to any disclaimer, the term of this patent is extended or adjusted under 35 U.S.C. 154(b) by 0 days.

(21) Appl. No.: 14/855,249

(22) Filed: Sep. 15, 2015

(65) Prior Publication Data

US 2016/0069918 A1    Mar. 10, 2016

Related U.S. Application Data (63) Continuation of application No. PCT/US2014/032092, filed on Mar. 27, 2014.
(Continued)

(51) Int. Cl.
*G01N 35/00* (2006.01)
*B01L 3/00* (2006.01)
(Continued)

(52) U.S. Cl.
CPC ........ *G01N 35/00732* (2013.01); *B01L 3/545* (2013.01); *G01N 35/0099* (2013.01);
(Continued)

(58) Field of Classification Search
CPC .. G01N 35/026; G01N 35/1065; G01N 35/10; G01N 35/00069; G01N 35/54306; G01N 35/54313; G01N 35/54366; G01N 35/00871; G01N 35/1011; G01N 35/00029; G01N 35/00623; G01N 35/1072; G01N 35/0092
See application file for complete search history.

(56) References Cited

U.S. PATENT DOCUMENTS

2002/0015665 A1* 2/2002 Lindsey ................. G01N 35/04
                                                                422/64
2002/0164779 A1   11/2002 Cocola et al.
(Continued)

FOREIGN PATENT DOCUMENTS

GB     2375487 A     11/2002
WO     2012004704 A1   1/2012
(Continued)

OTHER PUBLICATIONS

International Search Report and Written Opinion dated Sep. 25, 2014 for PCT/US2014/032092.

*Primary Examiner* — Christopher Adam Hixson (57) ABSTRACT

Systems and methods are provided for processing a biological sample. In one embodiment, the method comprises receiving a sample vessel containing the sample; retrieving information from an information storage unit associated with the sample; using said information for selecting at least one cartridge from at least two or more different cartridges, each configured for use with a sample processing device; loading at least one or more reagents onto the cartridge, wherein the one or more reagents to be added are selected based at least in part on the information or instructions derived from the information; and placing the sample vessel in the cartridge.

20 Claims, 5 Drawing Sheets

Related U.S. Application Data (60) Provisional application No. 61/805,925, filed on Mar. 27, 2013.

(51) Int. Cl.
    *G01N 35/02*         (2006.01)
    *G01N 35/10*         (2006.01)
    *G01N 35/04*         (2006.01)

(52) U.S. Cl.
    CPC ....... *G01N 35/021* (2013.01); *G01N 35/1002* (2013.01); *B01L 2200/16* (2013.01); *B01L 2300/021* (2013.01); *B01L 2300/022* (2013.01); *G01N 2035/00346* (2013.01); *G01N 2035/00752* (2013.01); *G01N 2035/00851* (2013.01); *G01N 2035/0436* (2013.01); *G01N 2035/0489* (2013.01); *Y10S 901/01* (2013.01); *Y10S 901/41* (2013.01)

(56) References Cited

U.S. PATENT DOCUMENTS

| | | | |
|---|---|---|---|
| 2009/0088336 A1* | 4/2009 | Burd | B01J 19/0046 506/9 |
| 2009/0130719 A1* | 5/2009 | Handique | B01L 3/5025 435/91.2 |
| 2009/0136386 A1 | 5/2009 | Duffy et al. | |
| 2011/0294205 A1 | 12/2011 | Hukari et al. | |

FOREIGN PATENT DOCUMENTS

| | | | |
|---|---|---|---|
| WO | 2012012779 | A2 | 1/2012 |
| WO | 2014160903 | A2 | 10/2014 |

\* cited by examiner

BIOLOGICAL SAMPLE PROCESSING

BACKGROUND

Analysis of biological samples from a subject may be important for health-related diagnosing, monitoring and/or treating of the subject. A variety of methods are known for the analysis of biological samples. However, in order to provide better diagnosing, monitoring, and/or treating of subjects, improvements in the analysis of biological samples are desired. Current techniques have various limitations, including but not limited to wasted reagents/materials, lack of flexibility in test menu, and/or low throughput/high cost associated with sample analysis.

INCORPORATION BY REFERENCE

All publications, patents, and patent applications mentioned in this specification are herein incorporated by reference to the same extent as if each individual publication, patent, or patent application was specifically and individually indicated to be incorporated by reference. However, in the event of a conflict between the content of the present express disclosure and the content of a document incorporated by reference herein, the content of the present express disclosure controls.

SUMMARY

The disadvantages associated with the prior art are overcome by at least some embodiments described herein.

In one embodiment, a method is provided for processing a biological sample, the method comprising: receiving a sample vessel containing the sample; retrieving information from an information storage unit associated with the sample; using said information for selecting at least one cartridge from at least two or more different cartridges, each configured for use with a sample processing device; loading at least one or more reagents onto the cartridge, wherein the one or more reagents to be added are selected based at least in part on the information or instructions derived from the information; and placing the sample vessel in the cartridge.

It should be understood that one or more of the following features may be adapted for use with any of the embodiments described herein. For example and not limitation, retrieving the information may comprise using optical scanning to obtain information from the information storage unit. Optionally, retrieving comprises using electromagnetic techniques to obtain information from the information storage. Optionally, the information storage unit is on the sample vessel. Optionally, the information storage unit is on the sample vessel and/or a test order. Optionally, the information storage unit comprises a bar code. Optionally, the information storage unit comprises a QR code. Optionally, the information storage unit comprises a radiofrequency-based storage unit. Optionally, the method comprises communicating the information from to an external device. Optionally, the method comprising receiving from the external device instructions for cartridge assembly. Optionally, the receiver may be a communications unit at or near the cartridge assembly location. Optionally, the information comprises cartridge assembly instructions. Optionally, the information comprises information regarding components that are to be included in the cartridge. Optionally, the information comprises information specifying which cartridge to select. Optionally, the information comprises information specifying which tests are to be performed on the sample. Optionally, at least one of the cartridges is partially loaded with some components prior to being selected. Optionally, at least one of the cartridges comprises a frame without other cartridge components prior to being selected for cartridge assembly. Optionally, at least one of the cartridges comprises a frame without other cartridge components therein prior to the cartridge being selected for cartridge assembly.

Optionally, the cartridge comprises at least one absorbent pad. Optionally, the two or more different cartridges each has a different configuration for holding the reagents. Optionally, the two or more different cartridges each defines one or more locations for receiving one or more reagent vessels. Optionally, the two or more different cartridges each defines one or more locations for receiving one or more diluent vessels. Optionally, the two or more different cartridges each defines one or more locations for receiving one or more pipette tips. Optionally, the two or more different cartridges each defines one or more locations for receiving one or more reaction vessels. Optionally, the two or more different cartridges each defines one or more locations for receiving one or more cuvettes. Optionally, the two or more different cartridges each defines one or more locations for receiving one or more arrays of reagents. Optionally, the two or more different cartridges each defines one or more locations for receiving one or more arrays of diluents. Optionally, the two or more different cartridges each defines one or more locations for receiving one or more arrays of pipette tips. Optionally, the two or more different cartridges each defines one or more locations for receiving one or more arrays of reaction vessels. Optionally, the two or more different cartridges each defines one or more locations for receiving one or more arrays of cuvettes. Optionally, the method comprises using one or more pick-and-place robots to add the reagents to the cartridge. Optionally, at least one robot is a delta robot. Optionally, at least one robot is a D3 delta robot. Optionally, at least one robot is a D4 delta robot. Optionally, at least one robot is a D5 delta robot. Optionally, at least one robot is a. D6 delta robot. Optionally, the robot is position in an overhead position over the cartridge assembly area.

Optionally, the cartridge has a structure that can be used to register the cartridge with the sample processing device for desired positioning of the cartridge. Optionally, this may be one or more protrusions on the cartridge. Optionally, this may be one or more indentations on the cartridge. Optionally, some embodiments may use a combination of the foregoing for registration purposes. Optionally, each of the two or more different cartridges has the structure to register the cartridge with the sample processing device. Optionally, the structure comprises an angled structure for alignment of the cartridge with a tray in the sample processing device. Optionally, a visual mark on the cartridge is used for positioning the cartridge in a cartridge receiving location of the sample processing device.

Optionally, the method comprises transporting the cartridge with the sample vessel and one or more reagents therein or thereon, from a cartridge assembly location to a sample processing location. Optionally, the method comprises transporting two or more cartridge simultaneously from a cartridge assembly location to a sample processing location. Optionally, the method comprises operably coupling the assembly location with the sample processing location with a transport assembly. Optionally, the transport assembly comprises a self-propelled robot configured to transport one or more cartridges from the assembly location to the sample processing location. Optionally, at least one end effector is on the robot for handling the cartridge. Optionally, at least one end effector for loading components into the cartridge. Optionally, the transport assembly comprises a conveyor-belt based system for transporting the cartridge. Optionally, the method comprises using a cartridge loading assembly to move a cartridge from the transport assembly to at least one sample processing device. Optionally, the method comprises using a cartridge loading assembly to move a cartridge from the transport assembly to cartridge receiving location for at least one sample processing device. Optionally, the method comprises using a cartridge loading assembly to move a cartridge from the transport assembly to one of a plurality of cartridge receiving locations that leads to one or more sample processing devices. Optionally, a plurality of sample processing devices are located at the processing location. Optionally, the sample processing devices are arranged in an array configuration. Optionally, the sample processing devices are arranged in a semi-circular array configuration about a cartridge loading assembly.

In one non-limiting example, a method is provided for processing a biological sample, the method comprising: retrieving information from an information storage unit associated with a cartridge configured for use with a sample processing device; loading; the cartridge comprising one or more reagents and the sample vessel into the sample processing device, wherein the loading comprises using a robotic manipulator mounted on a transport having a thermally controlled storage area housing a plurality of the cartridges, each cartridge having a sample from a different subject. Optionally, some embodiments may have cartridges that each contain at least two samples from the same subject, wherein each sample contains a different preparatory agent such as but not limited to different anti-coagulants.

Other goals and advantages of the methods, devices, and systems described will be further appreciated and understood when considered in conjunction with the following description and accompanying drawings. While the following description may contain specific details describing particular embodiments, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

It is noted that the drawings and elements therein are not necessarily drawn to shape or scale. For example, the shape or scale of elements of the drawings may be simplified or modified for ease or clarity of presentation. It should further be understood that the drawings and elements therein are for exemplary illustrative purposes only, and not be construed as limiting in any way.

DESCRIPTION OF THE SPECIFIC EMBODIMENTS

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by the values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

In some embodiments, provided herein are systems and methods for processing a biological sample.

Figure 1:
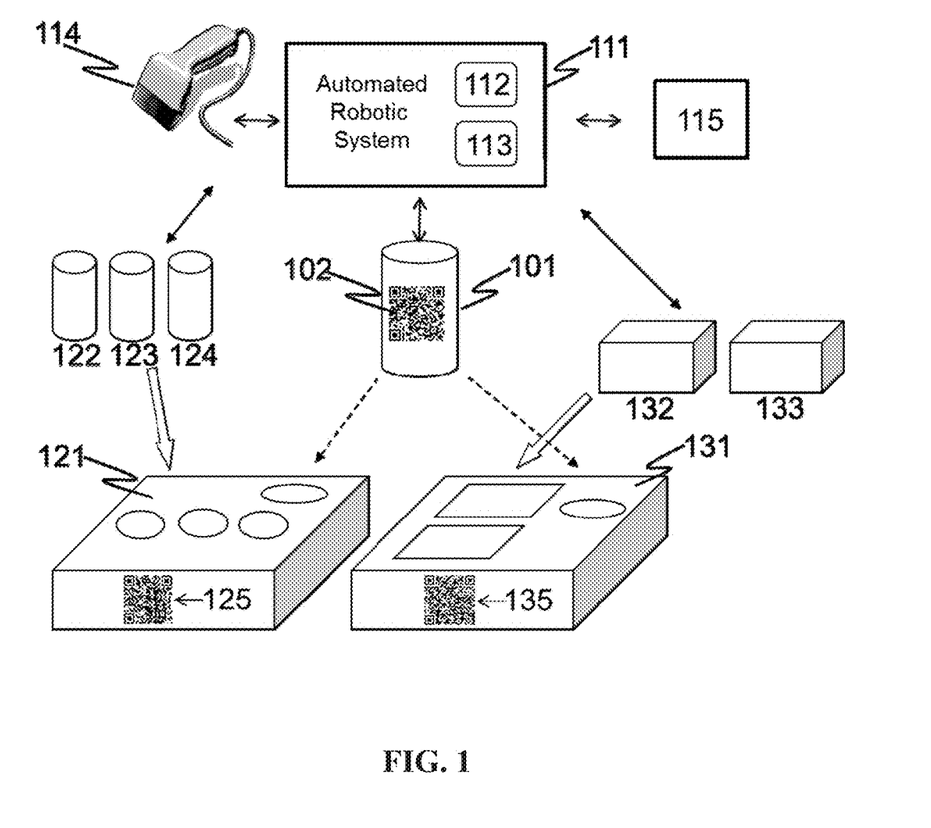
FIG. 1 shows an embodiment of a system provided herein.

In some embodiments, with reference to FIG. 1, a vessel 101 containing a sample such as but not limited to a biological sample may be positioned in or near an automated robotic system 111 configured for preparing cartridges for use with a sample processing device. In this non-limiting example, the vessel include an information storage unit such as but limited to labeling the cartridge with an identifier 102. The automated robotic system 111 may contain a local controller 112 and a communication assembly 113. The automated robotic system 111 may contain or be in communication with an identifier detector 114. The automated robotic system 111 may be in communication with an external device 115 via the communication assembly 113. The identifier detector 114 may detect the identifier 102 on the vessel 101. Based on information in the identifier 102, the local controller 112 may execute a protocol for the automated robotic system 111 to prepare a cartridge containing the vessel 101. The automated robotic system 111 may load the vessel 101 into a cartridge. The cartridge may be selected from a plurality of cartridges 121, 131. The automated robotic system 111 may further load one or more reagent-containing or empty vessels 122, 123, 124, 132, 133 into the cartridge containing the biological-sample containing vessel 101. A cartridge 121, 131 may be configured to receive certain reagents or vessels having certain shapes. For example, cartridge 121 may be configured to only receive vessels 122, 123, and 124, whereas cartridge 132 may be configured to only receive vessels 132 and 133. Prior to the loading of the biological sample-containing vessel 101 into the cartridge, the cartridges 121, 131 and reagent-containing and empty vessels 122, 123, 124, 132, 133 may be stored in the automated robotic system 111, or they may be stored near automated robotic system 111 such that they are accessible to the system 111. A cartridge 121, 131 may have at least one information storage unit such as but not limited to an identifier 125, 135 on the cartridges, respectively. Although this non-limiting example is shown loading the sample containing vessel 101 into the cartridge, it should be understood that some embodiments may load the sample containing vessel 101 into the cartridge at a later point in time, or in some alternative embodiments, not at all. Although this non-limiting example is shown loading one sample containing vessel 101 into the cartridge, other embodiments may load two or more sample containing vessels 101 into the cartridge. Optionally, some embodiments may have a single structure that may contain a plurality of sample containing vessels 101.

In a system or method described herein, a biological sample may be provided. The sample may include one or more fluid components. In some instances, solid or semi-solid samples may be provided. Optionally, the sample may be from a subject. A subject may be a human or an animal. The sample may include a bodily fluid, secretion, or tissue of a subject. The biological sample may be a bodily fluid, a secretion, or a tissue sample. Examples of biological samples may include but are not limited to, blood, serum, saliva, urine, gastric and digestive fluid, tears, stool, semen, vaginal fluid, interstitial fluids derived from tumorous tissue, ocular fluids, sweat, mucus, earwax, oil, glandular secretions, breath, spinal fluid, hair, fingernails, skin cells, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk or other excretions. Samples may be from a plant, microorganism (e.g. virus, bacteria), or other biological material.

In some embodiments, a biological sample may be in a vessel or other container. In some embodiments, a biological sample is in a vessel which has an interior volume of no greater than 200 ml, 100 ml, 50 ml, 40 ml, 30 ml, 20 ml, 10 ml, 5 ml, 4 ml, 3 ml, 2 ml, 1 ml, 900 µl, 800 µl, 700 µl, 600 µl, 500 µl, 400 µl, 300 µl, 200 µl, 100 µl, 75 µl, 50 µl, 40 µl, 30 µl, 20 µl, 10 µl, 5 µl, 4 µl, 3 µl, 2 µl, or 1 µl. In some embodiments, a biological sample is in a vessel having any of the features of a sample-containing vessel described in any of the documents incorporated by reference elsewhere herein.

In some embodiments, a vessel containing a biological sample may be labeled with information storage unit such as but not limited to an identifier. In one non-limiting example, the vessel may be but is not limited to vessel 101. The identifier may be any structure or system for conveying information, such as but not limited to a bar code, a formation of lines or shapes, a series of alphanumerical characters, a radio frequency tag, or a physical structure (e.g. raised bumps or depressions in a surface). In some embodiments, the identifier may contain a storage or memory device and can transmit information to an identifier detector. An identifier may contain or be linked to information relating to, for example, any one or more of the identity of the subject from whom the biological sample was obtained, the time, date, or location of collection of the sample from a subject, the healthcare provider who requested the assays to be performed on the biological sample, which assays are to be performed on the biological sample, the type of cartridge to use with the biological sample, vessels to load into the cartridge with the biological sample, or reagents to load into the cartridge with the biological sample. In some embodiments, any of the above information is provided in the identifier itself. In some embodiments, an identifier may contain a code or other information which may be processed by an appropriate program to reveal any of the above information. In some embodiments, more than one identifier or type of identifier may be included in a vessel. An identifier may be added to a vessel prior to a biological sample being added to the vessel. Alternatively, an identifier may be added to a vessel after the biological sample is added to the vessel.

In one non-limiting example, a biological sample may be positioned in or near an automated robotic system configured for preparing cartridges for use with a sample processing device. In some embodiments, a biological sample is collected at a remote location, and transported to the automated robotic system. In other embodiments, a biological is collected near the automated robotic system. In some embodiments, a biological sample may be collected or transported to an automated robotic system according to system or method as described in any of the documents incorporated by reference elsewhere herein.

In a system or method described herein, an automated robotic system configured for preparing cartridges for use with a sample processing device may be provided. In some embodiments, the automated robotic system may contain a local controller. The local controller may be configured to control the movement of one or more parts of the automated robotic system. The local controller may contain a local memory. The local memory may contain tangible computer readable media with code, instructions, language to perform one or more steps as described elsewhere herein. The local memory may store one or more protocols. The protocols may be generated locally on the automated robotic system, or may be received from an external source (e.g. a cloud-based database, a USB drive, etc.).

In some embodiments, an automated robotic system may contain a communication assembly. The communication assembly may be part of or may be in communication with the local controller. The communication assembly may be configured to communicate with an external device. In some embodiments, the communication assembly may be configured to wirelessly communicate with an external device (e.g. with Bluetooth or RTM technology). In some embodiments, the communication assembly may communicate with an external device via a cellular or satellite network.

In some embodiments, an automated robotic system may be in communication with an external device. In some embodiments, the external device can be a computer system, server, or other electronic device capable of storing information or processing information. In some embodiments the external device includes one or more computer systems, servers, or other electronic devices capable of storing information or processing information. In some embodiments, the external device can include more servers as are known in the art and commercially available. Such servers can provide load balancing, task management, and backup capacity in the event of failure of one or more of the servers or other components of the external device, to improve the availability of the server. A server can also be implemented on a distributed network of storage and processor units, as known in the art, wherein the data processing according to the present invention reside on workstations such as computers, thereby eliminating the need for a server. In some embodiments, an external device may be a cloud-computing based system.

In some embodiments, an automated robotic system may contain or be in communication with an identifier detector. An identifier detector may detect an identifier on a vessel containing a biological sample. For example, an identifier detector may be a bar-code scanner or an RFID reader. In some embodiments, an identifier detector may contain an LED that emits light which can interact with an identifier which reflects light and which can be measured by the identifier detector to determine information provided in the identifier. In some embodiments, the identifier detector may be in communication with the local controller of the automated robotic system, such that information relating to an identifier on a vessel is transmitted from the identifier detector to the local controller.

In some embodiments, the automated robotic system may be or may contain a pick-and-place robot. In one non-limiting example, the pick-and-place robot may be a delta robot. The pick-and-place robot may be or have one or more characteristics of a pick-and-place robot available from, for example, ABB, Inc. (Zurich, Switzerland), Bastian Solutions (Indianapolis, Ind.), Codian Robotics (Veenendaal, Netherlands), Yaskawa (Eschborn, Germany), or Oystar (Lorenz-strasse, Germany). Of course, it should be understood that other automation systems, methods, or devices, including those that may be developed in the future, are not excluded for use with system(s), methods, or devices described herein.

In some embodiments, an automated robotic system may contain or have physical access to one, two, three or more cartridges. The cartridges may be configured to support one or more different vessels, including biological sample-containing vessel, reagent-containing vessels, and empty vessels. Vessels may include, for example, tips, containers, cuvettes, assay units, reagent units, processing units etc. In some embodiments, an automated robotic system may contain or have physical access to one, two, three, four, five or more different types of cartridges having different configurations for supporting vessels. For example, one type of cartridge may have a configuration such that it can support 100 vessels which each hold a volume of 50 microliters, whereas another type of cartridge may have a configuration such that it can support 10 vessels which each hold a volume of 100 microliters and 20 vessels which each hold a volume of 200 microliters. In another example, one type of cartridge may have a configuration such that it can support three microscopy cuvettes and 10 pipette tips, whereas another type of cartridge may have a configuration such that it can support 8 nucleic acid amplification vessels and 20 pipette tips. In another example, one type of cartridge may have a configuration such that it can support hexagonal-shaped vessels, whereas another type of cartridge may have a configuration such that it can support round-shaped vessels. Of course, other numbers, not specifically enumerated above, may also be configured for use with the systems, devices, and methods described herein.

In some embodiments an automated robotic system may contain or have physical access to one, two, three or more empty or reagent-containing vessels. In some embodiments, the empty or reagent-containing vessels may have any of the characteristics of empty or reagent-containing vessels as described in any of the documents incorporated by reference elsewhere herein. In some embodiments, the reagent-containing vessels may contain antibodies, nucleic acids, enzymes, dyes, buffers, salts, chromogens, or other reagents for performing assays related to biological samples. In some embodiments, vessels may contain a mixture of more than one reagent. In some embodiments, an automated robotic system may contain or have physical access to 1, 2, 3, 4, 5, 10, 20, 30, 40, 50, 100, 150, 200, 300, 400, 500, 1000, or more reagents, alone or in combination. In some embodiments, the reagent-containing vessels may contain any of the reagents described in any of the documents incorporated by reference elsewhere herein.

In some embodiments, prior to being loaded into the automated robotic system or placed in the vicinity thereof, the cartridges do not contain any empty or reagent-containing vessels. In other embodiments, the cartridges are fully loaded with empty and reagent-containing vessels sufficient to perform one or more assays with a biological sample prior to being loaded into the automated robotic system or placed in the vicinity thereof. In other embodiments, the cartridges partially loaded with some empty or reagent-containing vessels prior to being loaded into the automated robotic system or placed in the vicinity thereof. In some embodiments, the cartridges are loaded with empty vessels prior to being loaded into the automated robotic system or placed in the vicinity thereof.

Optionally, the automated robotic system may contain a housing, and one or more components of the system described herein may be inside the housing.

In some embodiments, a vessel containing a biological sample is loaded into an automated robotic system configured for preparing cartridges for use with a sample processing device. In some situations, a vessel containing a biological sample may be manually loaded by a human into the automated robotic system. In other embodiments, an automated robotic system may be configured to transport a vessel containing a biological sample from outside the system into the automated robotic system. For example, an automated robotic system may contain a pick-and-place robot which is configured to pick up a biological sample which is positioned outside of the system, and to move it into the system.

In some embodiments, a single vessel containing a biological sample is loaded into an automated robotic system at a time. In other embodiments, multiple vessels containing biological samples may be loaded simultaneously into an automated robotic system. For example, a rack or other structure which supports multiple vessels (e.g. 2, 3, 4, 5, 10, 15, 20, 30, 40, 50, 100, or more) may be loaded into an automated robotic system, thereby simultaneously transporting multiple vessels into the system at a time.

Optionally, an identifier on a vessel containing a biological sample may be detected by an identifier detector when a vessel is outside or inside an automated robotic system.

In some embodiments, an automated robotic system may prepare a cartridge containing a vessel containing a biological sample, based on information present in the identifier on the vessel and obtained by the identifier detector. For example, an identifier detector may detect information in an identifier on a vessel, this information may be communicated to the local controller of an automated robotic system, and based on this information, and the local controller may execute a protocol stored in a local memory on the automated robotic system for preparing a cartridge containing the vessel. In another example, an identifier detector may detect information in an identifier on a vessel, this information may be communicated to the local controller of an automated robotic system, this information may be further communicated to an external device via the communication assembly of the automated robotic system, based on this information, the external device may transmit a protocol to local controller via the communication assembly, and the local controller may then execute the protocol from the external device for preparing a cartridge containing the vessel.

In some embodiments, based on a protocol to prepare a cartridge containing a biological sample-containing vessel, the automated robotic system may load the sample-containing vessel into a cartridge of a certain type, wherein the cartridge is selected from one, two, three, four, five or more different types of cartridges having different configurations for supporting vessels which are contained in or are physically accessible to the automated robotic system. A protocol may direct that a sample-containing vessel be loaded into a certain cartridge type for one or more reasons, such as: the types of assays that are to be performed with the biological sample, the types or shapes of vessels that are to be used with assays with the biological sample, the type of sample processing device that is to receive the cartridge containing the biological sample, or which specific sample processing device is to receive the cartridge containing the biological sample.

In some embodiments, based on a protocol to prepare a cartridge containing a biological sample-containing vessel, the automated robotic system may load the sample-containing vessel into a certain specific cartridge, wherein the cartridge is selected from 1, 2, 3, 5, 10, 20, 50, or more different specific cartridges which are contained in or are physically accessible to automated robotic system. A protocol may direct that a sample-containing vessel be loaded into a certain specific cartridge for one or more reasons, such as: the specific cartridge may contain an identifier with information related to the biological sample, the specific cartridge may be pre-loaded with one or more empty or reagent-containing vessels for performing one or more specific assays or a specific group of assays with the sample, or any of the reasons provided above for loading a biological sample-containing vessel into a certain type of cartridge.

In solve embodiments, based on a protocol to prepare a cartridge containing a biological sample-containing vessel, the biological sample-containing vessel is loaded into a cartridge before empty or reagent-containing vessels are loaded into the cartridge. In other embodiments, the biological sample-containing vessel is loaded into a cartridge after all empty or reagent-containing vessels for performing one or more assays of interest are loaded into the cartridge. In still other embodiments, the biological sample-containing vessel is loaded into a cartridge after some empty or reagent-containing vessels are loaded into the cartridge, but prior to the loading of all empty or reagent-containing vessels for one or more assays of interest into the cartridge. In some embodiments, cartridges are provided to an automated robotic system containing some or all of the empty or reagent-containing vessels for performing one or more selected assays with a biological sample pre-loaded in the cartridge. In other embodiments, cartridges are provided to an automated robotic system without any of the empty or reagent-containing vessels for performing one or more selected assays with a biological sample pre-loaded in the cartridge.

In some embodiments, based on a protocol to prepare a cartridge containing a biological sample-containing vessel, the automated robotic system may load one or more empty or reagent-containing vessels into a selected cartridge. The empty or reagent-containing vessels may be loaded by the automated robotic system into a selected cartridge prior to, during, or after the loading of the biological sample-containing vessel into the cartridge. 1, 2, 3, 4, 5, 10, 20, 30, 40, 50, 100, 150, 200, 300, 400, 500, or more different empty or reagent-containing vessels may be loaded into a selected cartridge by the automated robotic system. 1, 2, 3, 4, 5, 10, 20, 30, 40, 50, 100, 150, 200, 300, 400, 500 or more different empty or reagent-containing vessels may be loaded into a selected cartridge by the automated robotic system, wherein the empty or reagent-containing vessels are selected from 1, 2, 3, 4, 5, 10, 20, 30, 40, 50, 100, 150, 200, 300, 400, 500, 1000, 2000, 5000, or more different empty or reagent-containing vessels which are contained in or are physically accessible to automated robotic system. A protocol may direct that a one or more specific different empty or reagent-containing vessels be loaded into a certain specific cartridge for one or more reasons, such as: the assays to be performed with the biological sample in the cartridge or the specific cartridge or type of cartridge that is to receive the vessels.

In solve embodiments, before, during, or after the preparation of a cartridge containing a biological sample-containing vessel, the automated robotic system may add an identifier to the cartridge. The cartridge identifier may have any of the characteristics or contain any of the information described elsewhere herein for the identifier on the biological sample containing vessel. In addition or alternatively, the cartridge identifier may contain information regarding, for example, the time, date, or location of the addition of the biological sample to the cartridge, the assays to be performed with the cartridge, which type of sample processing device is to receive the cartridge, or which specific sample processing device is to receive the cartridge.

In some embodiments, a system or method provided herein may include a plurality of sample processing devices. In some embodiments, a sample processing device may be or may contain any of the features of sample processing devices as described in any of the documents incorporated by reference elsewhere herein. In some embodiments, the plurality of sample processing devices may contain at least 2, 3, 4, 5, 6, 7, 8, 9, 10, 15, 20, 30, 40, 50, 100 or more sample processing devices. The plurality of sample processing devices may be located close to each other. In some embodiments, all of the sample processing devices of the plurality of devices are within the same room or building. In some embodiments, all of the sample processing devices of the plurality of devices are within a contiguous area of 1, 2, 3, 4, 5, 10, 15, 20, 30, 50, 100, or 200 square meters or less.

In some embodiments, in a system or method provided herein including a plurality of sample processing devices, the system or method may include a transport assembly for transporting sample-containing cartridges to, from, into, or out of one or more sample processing devices. In some embodiments, a transport assembly may be or include a conveyor belt or similar structure. In some embodiments, a transport assembly may be or include a robot. In some embodiments, the robot may operate on a track or with the aid guide rail or similar structure. In some embodiments, the robot may operate without a track or guide rail. In some embodiments, the robot may be self-propelled. In some embodiments, a cartridge is fully loaded with vessels when the cartridge is loaded onto a transport assembly. In other embodiments, a cartridge requires one or more additional empty or reagent-containing vessels to be added to the cartridge before one or more selected assays may be performed with a biological sample with using vessels in the cartridge. In some embodiments, a cartridge is added to a transport assembly prior to a vessel containing the biological sample being loaded into the cartridge.

In some embodiments, a transport assembly may contain or be capable of supporting a plurality of sample-containing cartridges. By way of non-limiting example, a conveyor belt or a robot may contain or be capable of supporting 1, 2, 3, 4, 5, 10, 15, 20, 30, 50, 100 or more cartridges. In one embodiment, these cartridges may be transported in batch manner. Optionally, some may transport the cartridges in a sequential manner.

Figure 2:
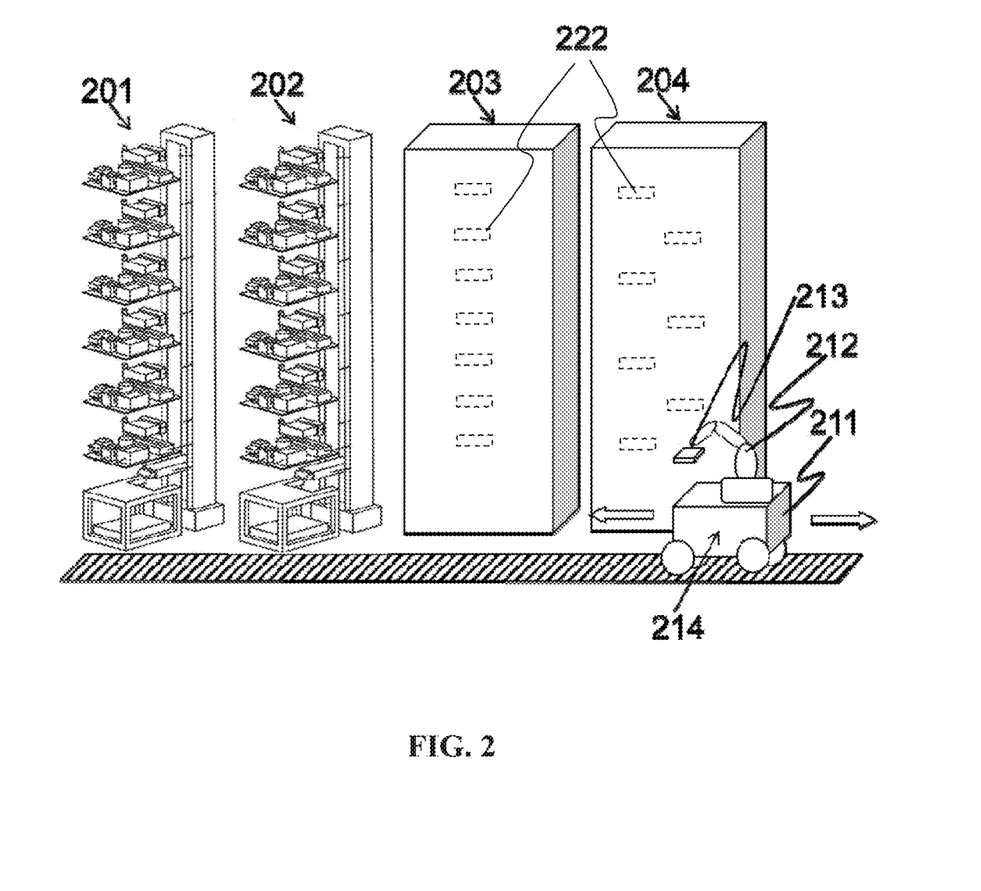
FIG. 2 shows an embodiment of a system provided herein.

In some embodiments, with reference to FIG. 2, a system or method provided herein may include a plurality of sample processing devices 201, 202, 203, 204. One or more devices of the plurality of sample processing devices 201, 202, 203, 204 may be adjacent to another of the sample processing devices 201, 202, 203, 204. One or more devices of the plurality of sample processing devices 201, 202, 203, 204 may have the same configuration as another of the sample processing devices 201, 202, 203, 204. One or more devices of the plurality of sample processing devices 201, 202, 203, 204 may have a different configuration as compared with another of the sample processing devices 201, 202, 203, 204. A transport assembly 211 may be present in the same room as the plurality of sample processing devices 201, 202, 203, 204. The transport assembly 211 may contain an end-effector 212 for moving a cartridge 213 into or out of a sample processing device 201, 202, 203, 204. The transport assembly 211 may further contain a storage area 214 for storing one or more new or used cartridges. It should be understood that although the images of the sample processing devices 201 and 202 are shown to be oriented at an angle to the path followed by the transport assembly 214 in FIG. 2, the devices 201 and 202 may also be oriented to be orthogonal to the path to facilitate alignment of a cartridge with a sample receiving location on the sample processing devices 201 and 202. It should also be understood that the sample receiving locations 222 on the sample processing devices may be aligned in a straight line, a pattern, or other manner as desired to facilitate one or more aspects of sample handling or processing.

It should also be understood that in some embodiments, the storage area 214 may be a thermally controlled storage area, which in one non-limiting example, may be used to begin acclimating the cartridges toward a desired temperature range. Optionally, some embodiments may use the thermally controlled storage area to begin incubation process(es) for one or more of the cartridges. It should be understood that within the thermally controlled storage area, there may be at least one region configured for at least one temperature range and at least one other region for at least one other temperature range. In one embodiment, each region can hold at least one cartridge. Optionally, some may have region(s) that hold at least two or more cartridges. Optionally, some embodiments may have each cartridge with its own individually controllable temperature zone. Optionally, some embodiments may be configured to control one portion of the cartridge(s) to one temperature while controlling a different portion of the same cartridge(s) to a different temperature. In one non-limiting example, a top portion of one area on the cartridge is exposed to a thermal environment to control that area to first temperature while a an underside portion of another are of the cartridge is exposed to a second thermal environment to control that area to second temperature different from the first temperature. In one embodiment, the storage area 214 may define a plurality of shelves, slots, or other cartridge holding areas which may be heated in zones or individually to a desired temperature range. In one embodiment, an information storage unit on or associated with the cartridge may provide temperature and/or other information regarding the cartridge. Some embodiments may use a pettier thermal device, resistive thermal device, phase-change thermal device, or the combinations thereof in the storage area or in each slot of the storage areas.

In one non-limiting example, the storage area 214 may be a removable device coupleable to the transport assembly 211 such that a plurality of cartridge may be loaded or unloaded at one time. In one non-limiting example, the storage area 214 may be thermally controlled package, backpack, hard-shelled container, soft-shelled container, partially soft-shelled container, single or multiple combinations of the foregoing, or other types of containers that may be implemented in the future. Some embodiments of the transport assembly 211 may be able to simultaneously transport two or more units having storage areas 214. Optionally, some embodiments of the transport assembly 211 may have a hopper, flexible conveyor, flexible delivery system, or a chute for receiving cartridges. Some embodiments may transport one large unit with a storage area 214 and a similar sized or smaller unit with a storage area controlled to a different temperature range. Some embodiments may have units with nested storage areas 214, perhaps with one controlled to a different temperature than the other to assist with accelerating processing. Some embodiments may include a vibration source (constant or periodic motion) to assist in pre-processing of the sample and/or cartridge while on-board the transport assembly 211. Optionally, some embodiments may include a controlled atmosphere in the storage area 214 to assist in preprocessing of the sample and/or to preserve the integrity of the sample or the cartridge. The control may be by pressure and/or the type of gas in the storage area 214. Optionally, some embodiments may have a separate transport assembly for sample vessels and another transport assembly for cartridges. Some embodiments may have a transport assembly with one storage area of samples and one for cartridges. Some embodiments may have cartridges being transported without sample vessels and the two are not combined until east before insertion into the sample processing device or they may be inserted separately into the sample processing device. Optionally, some embodiments of the transport assembly may have at least one storage area that is cooled below ambient for the sample vessels and at least one storage area heated to bring the cartridge to a processing temperature. Optionally, both storage areas may be controlled to be heated or cooled.

Optionally, a transport assembly may have a local controller, a communication assembly, and it may be capable of communicating with an external device. In some embodiments, the local controller, communication assembly, and external device may have any of the properties described elsewhere herein for the local controller, communication assembly, and external device of the automated robotic system. In some embodiments, the external device may be same external device with which the automated robotic system communicates.

Figure 3:
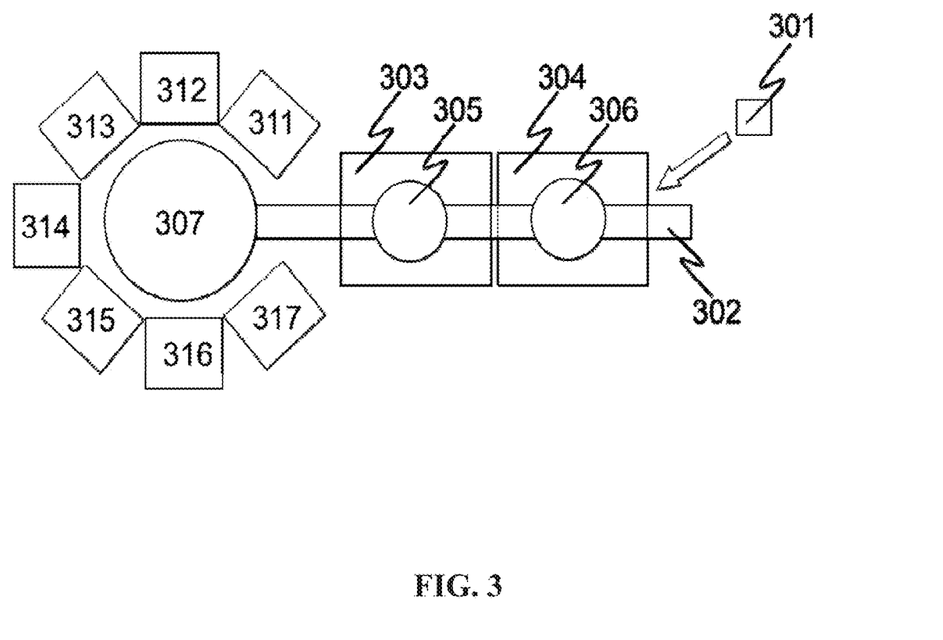
FIG. 3 shows an embodiment of a system provided herein.

In some embodiments, with reference to FIG. 3, a cartridge 301 may be introduced onto a transport assembly which includes a conveyor belt 302. The transport assembly may further contain one or more vessel loading stations 303, 304. Each vessel loading station 303, 304 may contain a pick-and-place robot 305, 306 (e.g. a delta robot) for loading vessels into the cartridge 301. The pick-and-place robot may be configured to load empty vessels, reagent-containing vessels, or biological sample-containing vessels into a cartridge 301. The cartridge 301 may be loaded with one or more vessels as it travels along the conveyor belt 302 so that as it reaches the end of the conveyor belt 302, it is loaded with all vessels and reagents necessary to perform one or more selected assays with a biological sample in the cartridge 301 in a sample processing device. In some embodiments, a plurality of sample processing devices 311, 312, 313, 314, 315, 316, 317 may be present in a system or method including a transport assembly which includes a conveyor belt 302. At the end of the conveyor belt, a cartridge loading assembly 307 may receive the loaded cartridge 301 from the conveyor belt 302. The cartridge loading assembly 307 may be configured to load a cartridge 301 into a sample processing device 311, 312, 313, 314, 315, 316, 317.

In some embodiments, in systems and method provided herein, an automated robotic system provided herein may be used with a transport assembly provided herein. For example, a vessel containing a biological sample may be provided at an automated robotic system and loaded into a cartridge as described herein. The cartridge may then be moved to a transport assembly, and from there loaded into a sample processing device. In some embodiments, one or more or all of these steps is automated, such that a biological sample may be analyzed according to systems and methods provided herein with minimal direct human intervention.

In some embodiments, a sample-containing vessel, cartridge, sample processing device, blood collection device, sample transport method, empty vessel, reagent-containing vessel, or reagents or may include or have any of the features of the sample-containing vessel, cartridge, sample processing device, blood collection device, sample transport method, empty vessel, reagent-containing vessel, or reagent described in any one or more of U.S. Pat. No. 8,088,593, U.S. patent application Ser. Nos. 13/244,947, 13/769,779, 13/769,817, 13/769,818, 13/769,820, U.S. Provisional Patent Application Nos. 61/766,076, 61/766,113, 61/766,117, 61/766,119, 61/697,797, 61/786,351, 61/733,886, all of which are herein incorporated by reference in their entirety for all purposes. U.S. Patent Application No. 61/805,925 is also fully incorporated herein by reference in its entirety for all purposes.

Figure 4:
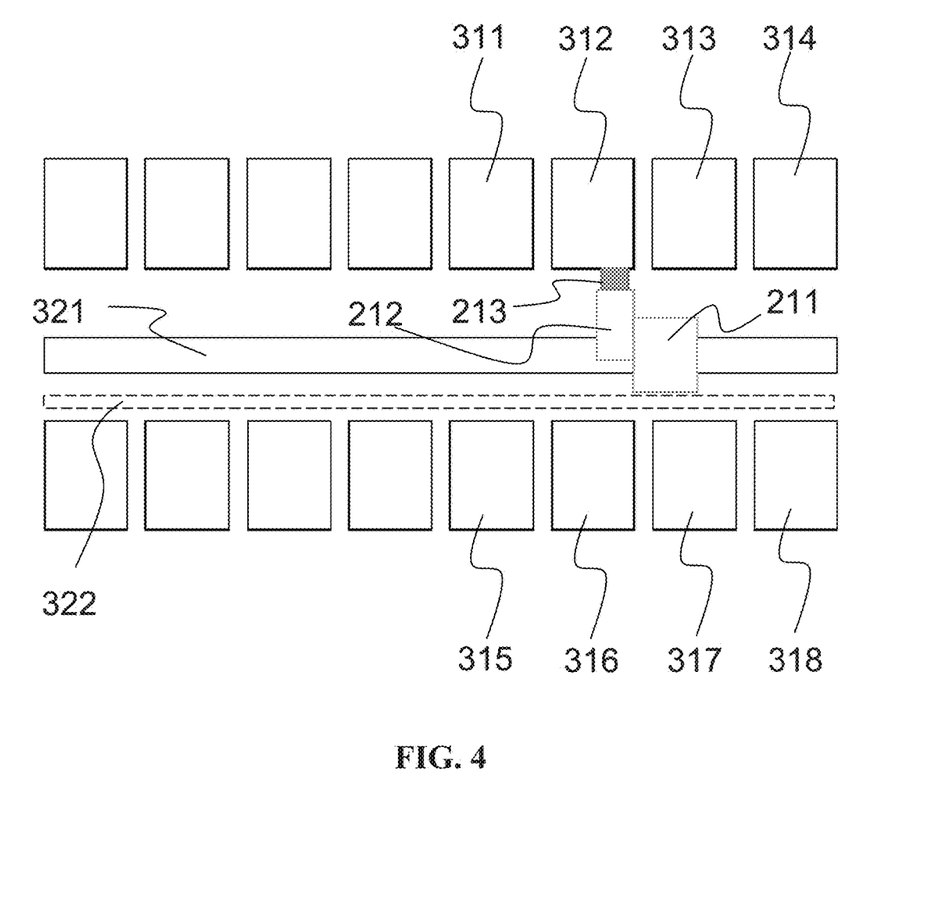
FIG. 4 shows an embodiment of a system provided herein.

FIG. 4 shows a still further non-limiting example wherein sample processing devices 311, 312, 313, 314, 315, 316, 317, and 318 may be on either side of the path 321 to be traveled by the transport assembly 211. This shows that the transport assembly 211 may be used to service sample processing devices on multiple sides of the transport assembly 211. Some embodiments may have the transport assembly 211 return to a base station separate from the sample processing devices for loading and/or unloading of cartridges. There may be a switch path to allow for multiple transport assemblies 211 to be moved onto the path 321. The switch may be at a hub such as but not limited to the base station wherein a turn table, switching track, or other device can allow for multiple transport assemblies 211 to be moved onto the same pathway. Optionally, some embodiments may not have a path but instead use a trackless surface wherein the transport assemblies have other guidance systems to travel along a designated path. Optionally, some may use vision, IR, and/or other systems to autonomously navigate to the correct location. Some embodiments may have transport assemblies operating along parallel "tracks" 321 and 322 in front of the two banks of sample processing devices.

Figure 5:
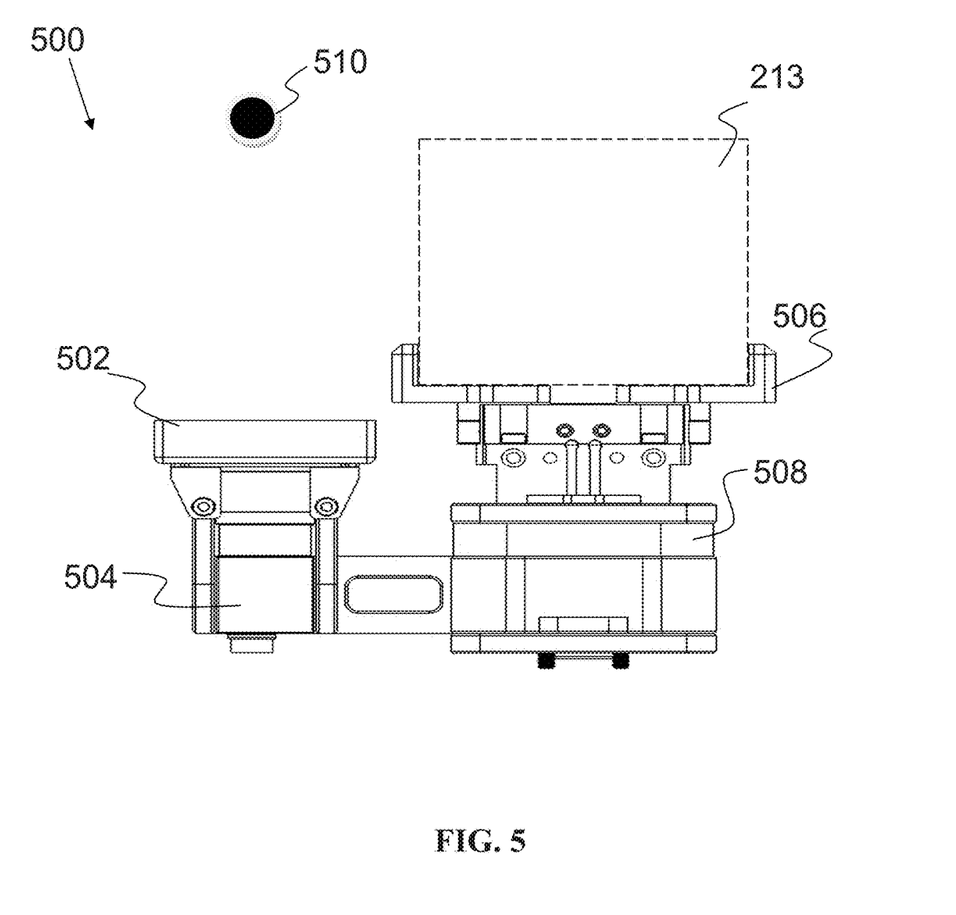
FIG. 5 shows an embodiment of a system provided herein.

Referring now to FIG. 5, a still further embodiment is shown of at least a portion of an end-effector that may be used with the transport assembly 211. FIG. 5 is a top-down view of the end effector 500 wherein it may be included as part of a robotic arm or other manipulator. This top-down view of this non-limiting example shows that there may be an illumination source 502 for use with a detector 504 such as but not limited to a camera (IR, visual, or other). This guidance system can be used to assist with positioning of jaw 506 of the end-effector 500 to engage a cartridge. It can also be used to align the end-effector 500 to allow insertion of the cartridge to a cartridge receiving location. Some embodiments may use an alignment guide to the side or adjacent area 510 to the cartridge receiving location that can act as a guide dot, fiducial, or other positioning landmark for alignment of the end-effector. In this non-limiting example, the jaw 506 may be replaced with a different type of manipulator depending on the shape of the cartridge to be handled. In some embodiments, the jaw 506 may have feature(s) shaped to be mating with feature(s) on the cartridge. Although the embodiment herein shows a vision system coupled to the end-effector, it should be understood that some embodiments may not have a vision system but instead uses a different guidance technique. Optionally, some embodiments may include a tool such as but not limited to rod, elongate member, flat spatula-type extension, extendable grips, or the like to assist with insertion and/or removal of a cartridge for a target location. Some embodiments may have more than one robotic arm on a transport assembly 211. Optionally, some embodiment may have more than one end-effector on each robotic arm.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. It should also be understood that while the invention provided herein has been described herein using a limited number of terms and phrases for purposes of expediency, the invention could also be described using other terms and phrases not provided herein which also accurately describe the invention. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. As used in the description herein and through the claims that follow, a first object described as containing "at least a portion" of a second object may contain the full amount of/the complete second object. As used in the description herein and throughout the claims that follow, the terms "comprise", "include", and "contain" and related tenses are inclusive and open-ended, and do not exclude additional, unrecited elements or method steps. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013-2014 Theranos, Inc.

What is claimed is:

1. A method for processing a biological sample, the method comprising:
   receiving a sample vessel containing the sample;
   placing the sample vessel in a cartridge;
   retrieving information from an information storage unit on the sample vessel;
   using an automated robotic system to prepare the cartridge for use with a sample processing device by using said information for loading at least one or more reagents onto the cartridge with the sample vessel, wherein the one or more reagents to be added are selected based at least in part on said information or instructions derived from said information; and
   using the automated robotic system to load the cartridge and the sample vessel onto a robotic transport assembly for operably coupling a cartridge assembly location with a sample processing location of the sample processing device, wherein the cartridge assembly location is separate from the sample processing location and the cartridge assembly location is not inside the sample processing device, wherein the robotic transport assembly further comprises a thermally controlled storage area housing a plurality of said cartridges, each cartridge having a sample from a different subject.

2. The method of claim 1 wherein retrieving comprises using optical scanning to obtain information from the information storage unit.

3. The method of claim 1 wherein retrieving comprises using electromagnetic techniques to obtain information from the information storage unit.

4. The method of claim 1 wherein adding one or more reagents comprises using one or more pick-and-place robots to add the reagents to the cartridge.

5. The method of claim 1 further comprising using a structure on the cartridge to register the cartridge with the sample processing device for desired positioning of the cartridge.

6. The method of claim 5 wherein said structure comprises an angled structure for alignment of the cartridge with a tray in the sample processing device.

7. The method of claim 1 further comprising using a visual mark on the cartridge for positioning the cartridge in a cartridge receiving location of the sample processing device.

8. The method of claim 1 further comprising using the transport assembly for transporting the cartridge having the sample vessel and one or more reagents from the cartridge assembly location to the sample processing location.

9. The method of claim 1 further comprising transporting two or more cartridge simultaneously from the cartridge assembly location to the sample processing location.

10. The method of claim 1 further comprising storing a plurality of cartridges and reagents at the cartridge assembly location.

11. The method of claim 10 wherein the transport assembly comprises a self-propelled robot configured to transport one or more cartridges from the assembly location to the sample processing location.

12. The method of claim 11 further comprising at least one end effector on the robot for handling the cartridge.

13. The method of claim 11 further comprising at least one end effector for loading components into the cartridge.

14. The method of claim 10 wherein the transport assembly comprises a conveyor-belt based system for transporting said cartridge.

15. The method of claim 11, wherein the transport assembly is configured to move along a path comprising a guide rail between the cartridge assembly location and the sample processing location.

16. The method of claim 10 further comprising using a robotic cartridge loading assembly to load the cartridge onto the transport assembly.

17. The method of claim 10 further comprising using a cartridge loading assembly to move a cartridge from the transport assembly to one of a plurality of cartridge receiving locations that leads to one or more sample processing devices.

18. The method of claim 9 further comprising a plurality of sample processing devices at the sample processing location.

19. A method for processing a biological sample, the method comprising:
retrieving information from an information storage unit associated with a cartridge, wherein the cartridge is configured for use with a sample processing device;
using an automated robotic system to prepare the cartridge for use with a sample processing device by using said information for selecting and loading at least one or more reagents onto the cartridge;
using a robotic manipulator on a robotic transport assembly for loading the cartridge comprising one or more reagents and a sample vessel into the robotic transport assembly for moving the robotic manipulator, wherein the robotic transport assembly further has a thermally controlled storage area housing a plurality of said cartridges, each cartridge having a sample from a different subject.

20. A method for processing a biological sample, the method comprising:
retrieving information from an information storage unit associated with a cartridge, wherein the cartridge is configured for use with a sample processing device;
using an automated robotic system to prepare the cartridge for use with a sample processing device by using said information for selecting and loading at least one or more reagents onto the cartridge; and
using a robotic manipulator on a robotic transport assembly for loading the cartridge comprising one or more reagents and a sample vessel into the robotic transport assembly for moving the robotic manipulator, wherein the robotic transport assembly further has a thermally controlled storage area housing a plurality of said cartridges, each cartridge having a sample from a different subject;
wherein at least one of said cartridges comprises pipette tips and nucleic acid amplification vessels.

* * * * *